United States Patent
Chuang et al.

(10) Patent No.: US 10,322,264 B2
(45) Date of Patent: Jun. 18, 2019

(54) SYSTEMS AND METHODS FOR USING A MICROCANNULA INTRODUCER FOR SKIN AND SOFT TISSUE AUGMENTATION

(71) Applicant: United Arab Emirates University, Al-Ain (AE)

(72) Inventors: Gary Chuang, Boston, MA (US); Hassan Galadari, Dubai (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 14/221,416

(22) Filed: Mar. 21, 2014

(65) Prior Publication Data
US 2015/0217089 A1     Aug. 6, 2015

Related U.S. Application Data

(60) Provisional application No. 61/934,072, filed on Jan. 31, 2014.

(51) Int. Cl.
*A61M 25/06*     (2006.01)
*A61M 5/32*      (2006.01)
(Continued)

(52) U.S. Cl.
CPC ........ *A61M 25/065* (2013.01); *A61M 5/3287* (2013.01); *A61B 2017/00792* (2013.01);
(Continued)

(58) Field of Classification Search
CPC ............ A61M 2039/0081; A61M 5/46; A61M 25/06; A61M 25/0612; A61M 25/065;
(Continued)

(56) References Cited

U.S. PATENT DOCUMENTS 3,437,788 A * 4/1969 Lingley ................. A61M 5/343
                                                219/162
3,840,008 A * 10/1974 Noiles ................. A61M 5/3286
                                                604/117
(Continued)

OTHER PUBLICATIONS

"Filter Funnel, Plastic." Anpros Pty Ltd. N.p., Apr. 19, 2013. Web. Jun. 26, 2015. <https://web.archive.org/web/20130419140215/http://www.anpros.com.au/laboratory-glassware-plasticware/filter-funnel-plastic/>.*

*Primary Examiner* — Bhisma Mehta
*Assistant Examiner* — James D Ponton
(74) *Attorney, Agent, or Firm* — Foley & Lardner LLP; Shabbi S. Khan

(57) ABSTRACT

The present disclosure is directed to a needle introducer. The needle introducer includes a needle guide and a cannula body coupled to the needle guide. The needle guide includes a flared head and a tapered neck. The needle guide forms a first channel extending from a first opening in the flared head to a second opening in the tapered neck. The cannula body includes a beveled tip at a distal end of the cannula body. The cannula body forms a second channel extending from a first opening in a proximal end of the cannula body to a second opening in the distal end of the cannula body. The cannula body is coupled to the needle guide via the tapered neck of the needle guide to connect the first channel to the second channel. The cannula body is configured to maintain an injection portal in the soft tissue.

14 Claims, 6 Drawing Sheets

(51) Int. Cl.
*A61B 17/00* (2006.01)
*A61B 17/34* (2006.01)
*A61M 5/158* (2006.01)

(52) U.S. Cl.
CPC ............... *A61B 2017/3405* (2013.01); *A61B 2017/3407* (2013.01); *A61M 5/3291* (2013.01); *A61M 2005/1585* (2013.01); *A61M 2205/195* (2013.01)

(58) Field of Classification Search
CPC ............ A61B 17/3403; A61B 17/3415; A61B 2017/3405; A61B 2017/3407
See application file for complete search history.

(56) References Cited

U.S. PATENT DOCUMENTS

| | | | | |
|---|---|---|---|---|
| 4,966,582 A * | 10/1990 | Sit | ........................ | A61M 39/04 604/263 |
| 5,147,308 A * | 9/1992 | Singer | ................ | A61B 17/3403 600/567 |
| 5,762,639 A * | 6/1998 | Gibbs | ........................... | 604/272 |
| 5,911,706 A * | 6/1999 | Estabrook et al. | ........... | 604/116 |
| 6,254,586 B1 * | 7/2001 | Mann | ................. | A61B 5/14865 206/365 |
| 7,122,042 B2 * | 10/2006 | LoRusso | ............... | A61M 1/008 604/117 |
| 7,744,568 B2 * | 6/2010 | Douglas et al. | ......... | 604/167.01 |
| 8,226,614 B2 * | 7/2012 | Turner et al. | ............. | 604/164.04 |
| 2002/0198509 A1 * | 12/2002 | Mikszta | ................. | A61K 39/12 604/500 |
| 2003/0158521 A1 * | 8/2003 | Ameri | ........................... | 604/117 |
| 2004/0176763 A1 * | 9/2004 | Foley | ................. | A61B 17/3417 606/60 |
| 2006/0116691 A1 * | 6/2006 | Bonacci | ................. | A61M 25/01 606/108 |
| 2006/0135973 A1 * | 6/2006 | Hawkins et al. | ............. | 606/167 |
| 2006/0206111 A1 * | 9/2006 | Young | .............................. | 606/44 |
| 2010/0130939 A1 * | 5/2010 | Voss | .................. | A61M 25/0009 604/167.03 |
| 2011/0288532 A1 * | 11/2011 | Faherty | ............. | A61M 25/0017 604/525 |
| 2011/0313357 A1 * | 12/2011 | Skutnik et al. | ................ | 604/151 |
| 2013/0123662 A1 * | 5/2013 | Hipp | ................... | A61B 10/025 600/564 |
| 2014/0005571 A1 * | 1/2014 | Vaillancourt | ....... | A61B 10/0233 600/567 |
| 2014/0171919 A1 * | 6/2014 | Blacker | ......................... | 604/528 |
| 2014/0207110 A1 * | 7/2014 | Jonas | ............................ | 604/510 |

* cited by examiner

SYSTEMS AND METHODS FOR USING A MICROCANNULA INTRODUCER FOR SKIN AND SOFT TISSUE AUGMENTATION

CROSS-REFERENCE TO RELATED APPLICATION

The present application claims priority to U.S. Provisional Patent Application No. 61/934,072, filed Jan. 31, 2014 and entitled "SYSTEMS AND METHODS FOR USING A MICROCANNULA INTRODUCER FOR SKIN & SOFT TISSUE AUGMENTATION," which application is incorporated herein by reference in its entirety.

TECHNICAL FIELD

The present application relates generally to the field of medical injections. More specifically, the present application relates to systems and methods for introducing an injector to facilitate injections of one or more filler materials into a patient.

BACKGROUND

Medical procedures, such as skin augmentation generally achieved by injecting substances such as fillers into a patient's body, for example in the face of a patient, may require multiple injections at distinct injection sites in the patient's face. Multiple needle entries may be painful and at times may result in bruising, the magnitude and likelihood of which increase with increasing injections. The advent of microcannulas reduces pain and bruising. However, microcannulas may be blunt and/or may be flexible, thereby possibly requiring creation of an entry point prior to every insertion.

SUMMARY

The inventors have appreciated that reduced injection sites may be facilitated through the use of an introducer system. In view of the foregoing, the present disclosure is directed to, systems and methods for facilitating multiple injections via maintenance of a single injection portal.

Exemplary inventive embodiments provide a needle introducer for introducing an injector, also referred to herein as a needle for soft tissue augmentation. The needle introducer includes a needle guide and a cannula body coupled to the needle guide. The needle guide includes a flared head and a tapered neck. The needle guide forms a first channel extending from a first opening in the flared head to a second opening in the tapered neck. The cannula body includes a beveled tip at a distal end of the cannula body. The cannula body forms a second channel extending from a first opening in a proximal end of the cannula body to a second opening in the distal end of the cannula body. The cannula body is coupled to the needle guide via the tapered neck of the needle guide to connect the first channel to the second channel. The cannula body is configured to maintain an injection portal in the soft tissue to receive a needle cannula extending through the first and second channel into the soft tissue for a plurality of soft tissue augmentation injections.

In particular embodiments, the flared opening has a diameter larger than the cannula body. The cannula body may be composed of steel. The cannula body and the needle guide are composed of plastic, in accordance with particular embodiments. The cannula body may have a length of 2-10 mm. In particular embodiments, the cannula body includes a 22-30 gauge shaft. The cannula body may have a wall thickness of 300 microns. The cannula body is coupled to the needle guide by a friction fit, in accordance with particular embodiments. The cannula body may be coupled to the needle guide via an adhesive. In particular embodiments, the injector is removably coupled to the needle introducer via a sliding actuator. The sliding actuator may include a folding arm. In particular embodiments, the injector includes at least one of a syringe. a microcannula, and a blunt-tipped needle. The needle introducer includes a cap removably coupled to the beveled tip of the cannula body, in accordance with particular embodiments. The needle guide may include curved finger grips.

Other exemplary inventive embodiments provide a method of using a needle introducer for soft tissue augmentation. The method includes inserting a needle introducer through a skin surface and into the soft tissue to create an injection portal into the soft tissue for a plurality of soft tissue augmentation injections. The inserted needle introducer includes a needle guide and a cannula body coupled to the needle guide. The needle guide includes a flared head and a tapered neck. The needle guide forms a first channel extending from a first opening in the flared head to a second opening in the tapered neck. The cannula body includes a beveled tip at a distal end of the cannula body. The cannula body forms a second channel extending from a first opening in a proximal end of the cannula body to a second opening in the distal end of the cannula body. The cannula body is coupled to the needle guide via the tapered neck of the needle guide to connect the first channel to the second channel. The cannula body is configured to maintain an injection portal in the soft tissue to receive a needle cannula extending through the first and second channel into the soft tissue for a plurality of soft tissue augmentation injections. The method also includes inserting a first needle cannula into the needle introducer and through the injection portal. The first needle cannula extends beyond the beveled tip of the cannula body. The method further includes injecting a filler into the soft tissue via the first needle cannula, removing the first needle cannula from the needle introducer, and maintaining the injection portal in the soft tissue after removal of the first needle cannula from the needle introducer for a second injection.

In particular embodiments, the method also includes inserting a second needle cannula into the needle introducer and through the injection portal for the second injection. The second needle cannula extends beyond the beveled tip of the cannula body. The method may also include injecting a second filler into the soft tissue via the second needle cannula. In particular embodiments, the first needle cannula includes a blunt tipped needle cannula.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings are primarily for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and embodiments of, inventive systems, methods and apparatus for introducing a needle through a surface. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Figure 1:
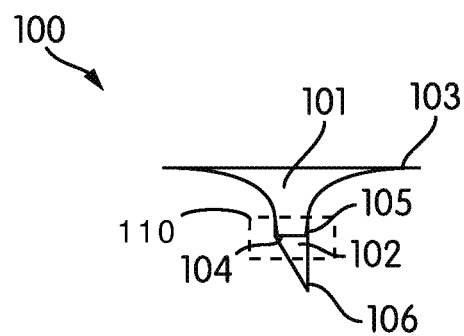
FIG. 1 illustrates a side view of a needle introducer for introducing an injector for soft tissue augmentation, in accordance with exemplary inventive embodiments.

FIG. 1 illustrates a side view of a needle introducer for introducing an injector for soft tissue augmentation, in accordance with exemplary inventive embodiments. The needle introducer illustrated in FIG. 1 includes introducer 100. Introducer 100 is configured to facilitate insertion of an injector, such as needle cannula, into a site. As discussed further herein, once the introducer 100 is inserted into a site the introducer 100 maintains an opening that provides a portal for a plurality of injectors, including, but not limited to microcannulas/needles, to be inserted through at temporally distinct periods. For example after the introducer 100 pierces the skin of a patient, the introducer remains in place and a microcannula/needle or syringe may be introduced through the skin via the portal provided by the introducer 100. Once the microcannula is in place, the introducer may be retracted along the length of the micro-cannula, to leave as much flexibility to the microcannula. To remove the microcannula and keep the portion in the skin open, the introducer can slide along the shaft of the microcannula within the skin, for example, while a physician changes syringes and a second microcannula/needle or syringe containing a substance such as a filler, which may be the same and or distinct from the substance injected via the first syringe, is introduced through the skin via the portal provided by the introducer 100. The introducer includes a cannula body portion 102 having a pointed or beveled tip 106 (shown as 206 in FIGS. 2 and 6) disposed at a distal end of the cannula body portion 102. The introducer also includes a needle guide portion 101 coupled to the cannula body portion 102 at a proximal end 104 of the cannula body portion 102. The needle guide portion 101 includes a flared head 103 that tapers into neck portion 105 coupled to the proximal end 104 of cannula body portion 102. The flared opening formed by the needle guide 101 is in fluid communication with the cannula body portion 102. In accordance with exemplary embodiments, the needle guide portion 101 may be coupled to the cannula body portion 102 via a friction fit, bonding, an adhesive, or other similar connection configurations (generally shown as box 110). In various embodiments, the cannula body portion 102 may be fitted with a hub configured to couple the cannula body portion 102 to the needle guide portion 101. In exemplary embodiments, the needle guide portion 101 and the cannula body portion 102 may be composed of distinct materials. For example the needle guide portion may be composed of a one material, such as plastic and the cannula body portion 102 may be composed of another material, such as stainless steel. In some embodiments, the introducer including the needle guide portion may be made of the same material, such as plastic, aluminum or steel.

In accordance with exemplary embodiments, the introducer 100 may have a total length of 1-0.5 cm. In accordance with illustrative embodiments, the cannula body portion 102 may be 1-10 mm deep, lengths permitting 1-2 mm penetration into the skin, which depths are sufficient for skin augmentation via fillers. The cannula body portion 102 may include an 18-30 gauge shaft having a hollow inner diameter and may have a wall thickness on the order of 10-500 microns. The needle guide portion 101 may be shaped in a cone-like or funnel shape as shown in the illustrated embodiments wherein the head 103 of the needle guide portion 101 may be flared radially outward and is composed of a plastic configured in a thin layer.

Figure 2:
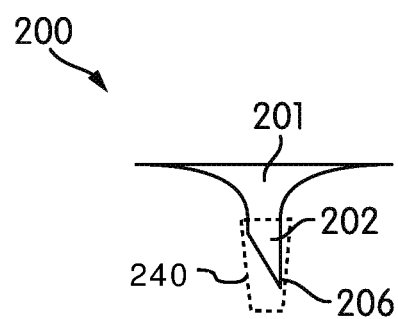
FIG. 2 illustrates a side view of a needle introducer for introducing an injector for soft tissue augmentation, in accordance with exemplary inventive embodiments.

FIG. 2 illustrates a side view of a needle introducer for introducing an injector for soft tissue augmentation, in accordance with exemplary inventive embodiments. FIG. 2 illustrates an introducer 200 that may be composed as an integral unit, for example composed of a single material, such as a hard plastic or other polymer providing sufficient rigidity such that short thin walled cannula body portion 202 is capable of piercing the skin while being composed of the same material as the needle guide portion 201. In various embodiments, cannula body portion 202 may be covered with a cap 240, such as a plastic cap to help prevent inadvertent punctures. Introducer 200 may advantageously reduce costs and may simplify manufacturing, through its unitary design.

Figure 3:
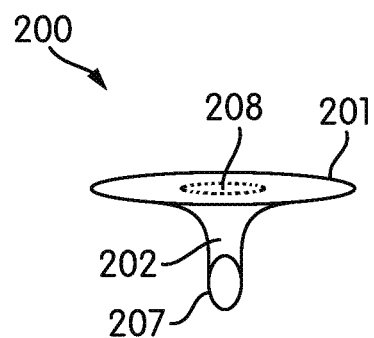
FIG. 3 shows a perspective view of the needle introducer of FIG. 2.

FIG. 3 shows a perspective view of the needle introducer of FIG. 2. As shown in FIG. 3, introducer 200 includes an opening 208 in the needle guide portion 201 and an opening 207 in the cannula body portion 202, which openings are in fluid communication with one another.

Figure 4:
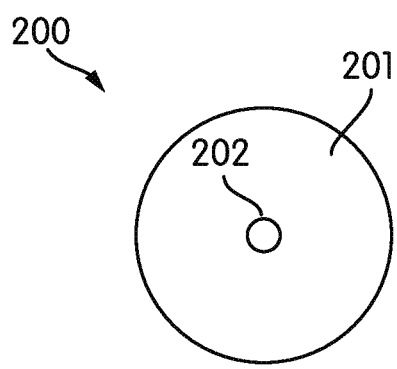
FIG. 4 illustrates a top view of the needle introducer of FIG. 2.

FIG. 4 illustrates a top view of the needle introducer of FIG. 2.

Figure 5:
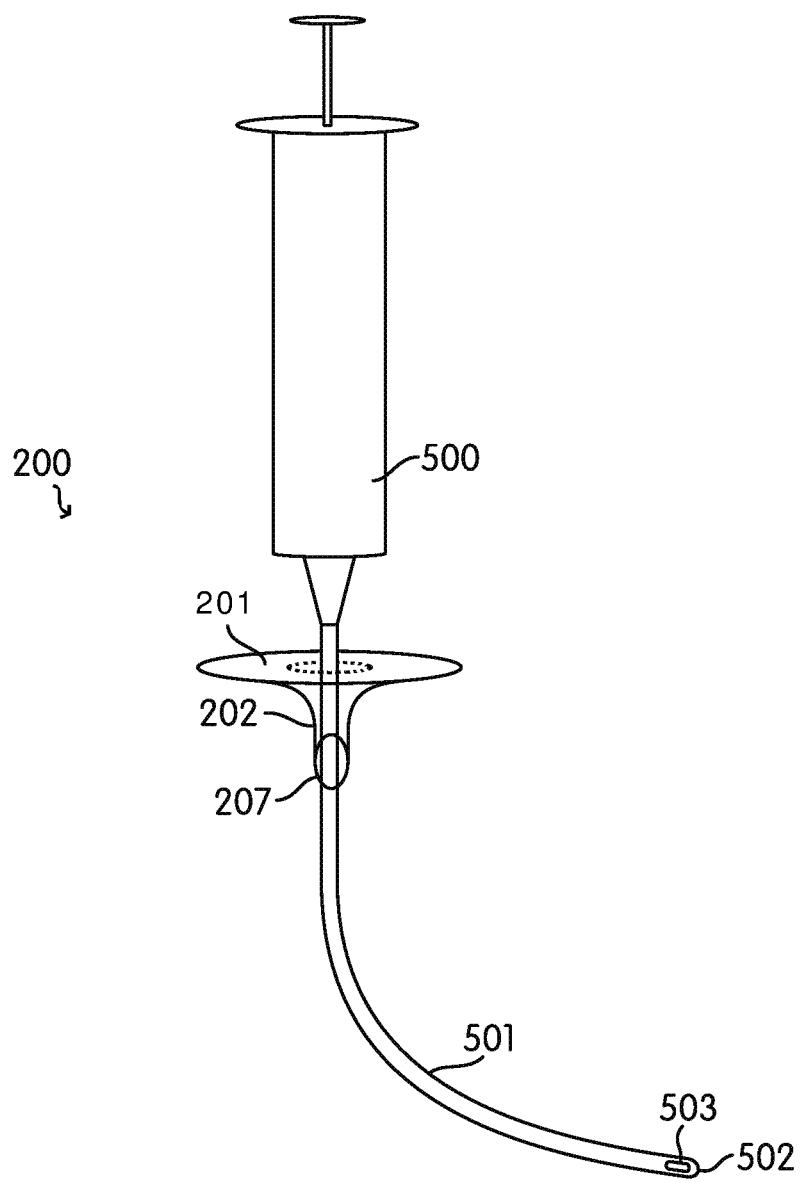
FIG. 5 demonstrates the needle introducer of FIG. 2 having an injector needle disposed therein.

FIG. 5 demonstrates the needle introducer of FIG. 2 having an injector needle disposed therein. In accordance with exemplary embodiments, the introducer 200 may facilitate use with an injection needle such as injector 500 having a microcannula 501 with an opening 503 positioned at a blunt or rounded tip 502 of the microcannula 501. Opening 207 includes an interior diameter sufficient to receive cannula 501, which may be on the order of 22 gauge to 30 gauge. Injectors, such as injector 500 having a microcannula having a blunt tip 502 may be advantageously used with exemplary embodiments of introducers disclosed herein as such microcannulas may have the flexibility and length to reach a plurality of regions, for example on the face, from a single portal created and maintained by the introducer 200 without traumatizing the underlying nerves, blood vessels etc. disposed under the skin. Accordingly, different fillers may be introduced via different needles, and introducer 200 will maintain the appropriate portal for introducing the different needles as the fillers and/or needles used are changed.

Figure 6:
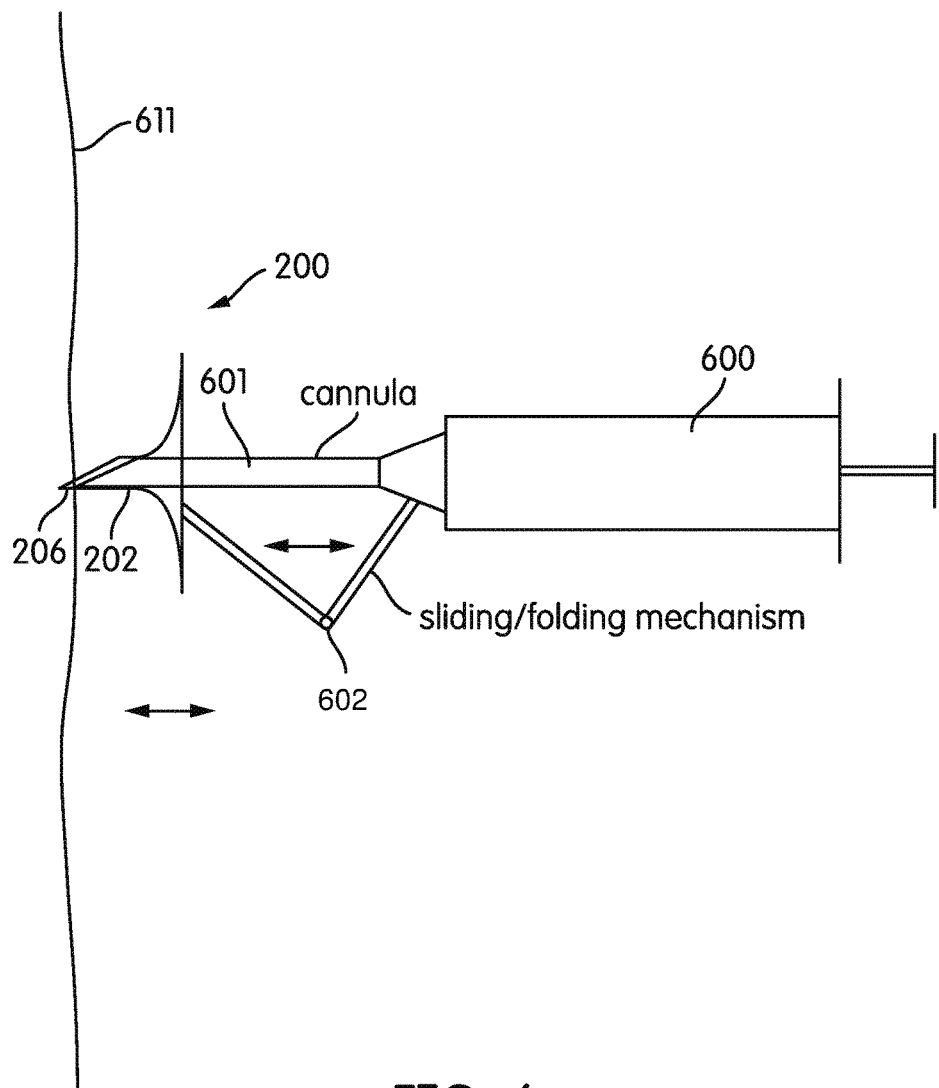
FIG. 6 shows a side view of a needle introducer coupled to a injector needle via a sliding actuator.

FIG. 6 shows a side view of a needle introducer coupled to a injector needle via a sliding actuator. The sliding mechanism 602 is coupled to injector 600 and to introducer 200 to guide introducer 200 with respect to injector 600 along cannula 601 of injector 600 to be able to re-insert or retract the introducer 200 with respect to the surface of the patient's skin. The sliding mechanism 602 may include an arm that folds to retract the introducer from the skin and thereby move the introducer closer to injector 600 along cannula 601. Sliding mechanism 602 may be removably coupled to introducer 200. Introducer 200 may include a hub, dock, or other interlocking mechanism for coupling sliding mechanism 602 thereto.

Figure 7:
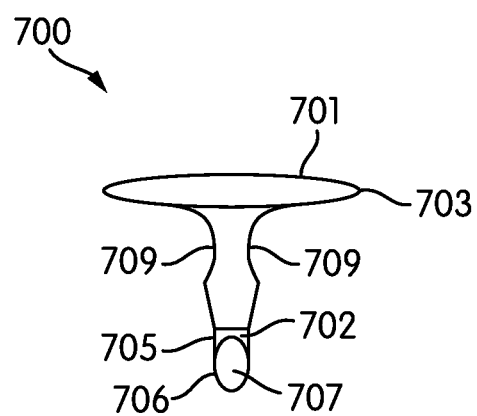
FIG. 7 illustrates a side view of another embodiment of a needle introducer, in accordance with exemplary inventive embodiments.

FIG. 7 illustrates a side view of another embodiment of a needle introducer, in accordance with exemplary inventive embodiments. Introducer 700 may include finger grips 709 contoured to follow the curves of a user's fingers. The finger grips 709 may be an integral part of needle guide portion 701. While finger grips 709 provide a gripping surface and fraction for the fingers, head 703 shields the fingers from the cannula of a needle being introduced into introducer 700. Introducer 700 includes cannula body portion 702 coupled to the needle guide portion 701 at the proximal end 705 of the cannula body portion 702, opposite the beveled end 706 disposed at a distal end of cannula body portion 702 and including opening 707.

Figure 8:
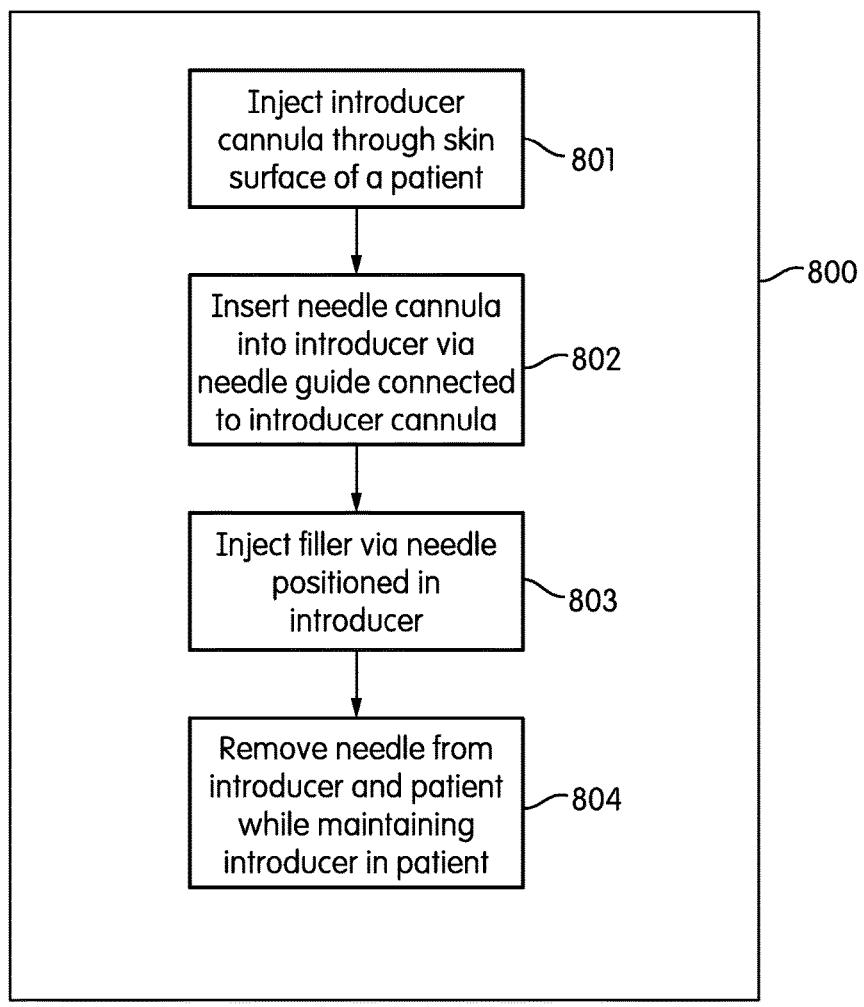
FIG. 8 provides a flow chart illustrating implementation of a needle introducer for introducing an injector for soft tissue augmentation, in accordance with exemplary inventive embodiments.

FIG. 8 provides a flow chart illustrating implementation of a needle introducer for introducing an injector for soft tissue augmentation, in accordance with exemplary inventive embodiments. Flow chart 800 demonstrates an exemplary implementation of using a needle introducer, such as introducer 100, for soft tissue augmentation. In process 801, a user, such as a physician, inserts a cannula body portion of a needle introducer through a first surface, such as a skin surface of a patient, via a beveled tip of the cannula body portion. The cannula body portion of the needle introducer is inserted such that the cannula body portion of the needle introducer penetrates the skin and the needle guide portion of the needle introducer remains outside of the skin adjacent to the skin surface. In process 802, a portion of an injector such as a microcannula, and more specifically the tip portion of the microcannula is inserted into the introducer via the needle guide portion such the microcannula is positioned within the introducer shaft. Because the cannula body portion of the needle introducer has pierced the skin of the patient and provides a portal through the skin surface of the patient, the microcannula introduced via the portion provided by the needle introducer may be blunt or rounded as it is not required to pierce the skin surface. In process 803 a filler, may be injected into the patient via the microcannula, needle, or other injector positioned in the needle introducer. Once the injection is properly administered and distributed in the patient, the microcannula may be removed from the skin in process 804 while the introducer remains in the patient and maintains the portal through the patient skin for any subsequent injections via the same microcannula, or another microcannula, needle or other injection that may include a distinct filler.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of the introducer or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to various embodiments. Other substitutions, modifications, changes and omissions may also be made in the design, operating conditions and arrangement of the various exemplary embodiments without departing from the scope of the present disclosure.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, describes techniques, or the like, this application controls.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in any claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive options (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in any claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In any claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An injector and a needle introducer for introducing the injector for soft tissue augmentation, the needle introducer comprising:

a needle guide having a flared head and a tapered neck, the needle guide forming a first channel that flares continuously from a second opening at a distal end of the tapered neck to a first opening defined by an exposed top edge of the needle guide; and a cannula body extending from a proximal end to a distal end, the proximal end integral to the needle guide, the cannula body having a beveled tip at the distal end of the cannula body, the cannula body forming a second channel extending from a first opening in the proximal end of the cannula body to a second opening in the distal end of the cannula body, the proximal end of the cannula body coupled to the needle guide via the distal end of the tapered neck of the needle guide such that the first channel and the second channel are in fluid connection, the cannula body including a wall extending from the proximal end of the cannula body to the beveled tip at the distal end, the wall having a uniform external diameter from the proximal end of the cannula body to the distal end of the cannula body, the cannula body configured to maintain an injection portal in the soft tissue to receive a needle cannula of the injector extending through the first and second channels into the soft tissue for a plurality of soft tissue augmentation injections, wherein an entire length extending from the proximal end of the cannula body to the distal end of the cannula body is insertable into the soft tissue and wherein the length of the cannula body is from 1 mm to 10 mm;

wherein the cannula body and the needle guide integrally form the needle introducer as a single unitary body and wherein the needle introducer is slidingly coupled to the needle cannula to allow retraction from, or reinsertion to, the injection portal along the needle cannula.

2. The injector and needle introducer of claim 1, wherein the first opening of the first channel has a diameter larger than a diameter of the cannula body.

3. The injector and needle introducer of claim 1, wherein the cannula body is composed of steel.

4. The injector and needle introducer of claim 1, wherein the cannula body and the needle guide are composed of plastic.

5. The injector and needle introducer of claim 1, wherein the cannula body has a length of 2-10 mm.

6. The injector and needle introducer of claim 1, wherein the cannula body includes an 18-30 gauge shaft.

7. The injector and needle introducer of claim 1, wherein the cannula body has a wall thickness of 10-500 microns.

8. The injector and needle introducer of claim 1, wherein the injector is removably coupled to the needle introducer via a sliding actuator.

9. The injector and needle introducer of claim 8, wherein the sliding actuator includes a folding arm.

10. The injector and needle introducer of claim 8, wherein the injector includes a syringe.

11. The injector and needle introducer of claim 8, wherein the needle cannula includes a microcannula.

12. The injector and needle introducer of claim 8, wherein the needle cannula includes a blunt-tip needle.

13. The injector and needle introducer of claim 1, further comprising a cap removably coupled to the beveled tip of the cannula body.

14. The injector and needle introducer of claim 1, wherein the needle guide includes curved finger grips.

* * * * *